United States Patent [19]

Siren et al.

[11] Patent Number: 5,284,839
[45] Date of Patent: Feb. 8, 1994

[54] USE OF INOSITOLTRISPHOSPHATE TO TREAT ABNORNAL GASTROINTESTINAL MOTILITY AND SECRETION

[75] Inventors: Matti Siren, Helsinki, Finland; Lars Edvinsson, Lund, Sweden

[73] Assignee: Perstorp AB, Sweden

[21] Appl. No.: 966,035

[22] PCT Filed: Jun. 19, 1991

[86] PCT No.: PCT/SE91/00439
§ 371 Date: Feb. 11, 1993
§ 102(e) Date: Feb. 11, 1993

[87] PCT Pub. No.: WO92/00079
PCT Pub. Date: Jan. 9, 1992

[30] Foreign Application Priority Data

Jun. 28, 1990 [SE] Sweden .................. 9002278-1

[51] Int. Cl.$^5$ .................................. A61K 31/66
[52] U.S. Cl. ........................................ 514/103
[58] Field of Search .............................. 514/103

[56] References Cited

U.S. PATENT DOCUMENTS

| 4,735,936 | 4/1988 | Siren | 514/103 |
| 4,777,134 | 10/1988 | Siren | 514/103 |
| 4,797,390 | 1/1989 | Siren | 514/103 |

FOREIGN PATENT DOCUMENTS

| 179439 | 4/1986 | European Pat. Off. . |
| 359257 | 3/1990 | European Pat. Off. . |

*Primary Examiner*—S. J. Friedman
*Attorney, Agent, or Firm*—Scully, Scott, Murphy & Presser

[57] ABSTRACT

The present invention relates to the use of inositoltrisphosphate (IP$_3$) for the preparing of a medicament effective as a neuropeptide Y- (NPY-) antagonist and to a pharmaceutical composition comprising at least one specific isomer of IP$_3$ and a pharmaceutically active compound effective in the cardiovascular, renal and/or cerebral area.

14 Claims, No Drawings

USE OF INOSITOLTRISPHOSPHATE TO TREAT ABNORMAL GASTROINTESTINAL MOTILITY AND SECRETION

The present invention relates to the use of at least one isomer of inositoltrisphosphate ($IP_3$) for the preparing of a medicament effective as a neuropeptide Y- (NPY-) antagonist and to a pharmaceutical composition comprising at least one specific isomer of $IP_3$ and a pharmaceutically active compound effective in the cardiovascular, renal and/or cerebral area.

Neuropeptide Y (NPY) is a peptide present in the central and peripheral nervous system. The peptide co-exists with noradrenaline in many neurons and acts as a neurotransmittor per se or synergistically together with noradrenaline. NPY-containing fibres are numerous around arteries especially for arteries in the heart but also arteries in the respiratory tract, the gastrointestinal tract and genitourinary tract. NPY is also present in the cerebrum with effects on e.g. blood pressure and release of different hormones.

NPY per se has vasoconstrictor effects, i.e. there is observed an increased blood pressure, local vasoconstriction and reduced heart rate when the substance is infused to animals.

NPY belongs to the pancreatic polypeptide (PP) family which also includes for example peptide YY (PYY).

In man and animals abnormal NPY-levels are associated with for example the following diseases or conditions:

Diseases pertaining to the vascular system, the heart, blood vessels and the peripheral circulation such as vasospasm, angina, hemorrhage, high blood pressure, cardiac hypertrophy, congestive heart failure and myocardial infarction;

Diseases pertaining to the renal system such as abnormal renal conditions like impaired flow of fluid and renal failure;

Cerebral diseases and diseases related to the central nervous system such as stroke and conditions associated with stroke, cerebral vasospasm and hemorrhage and depression;

Abnormal drink and food intake such as obesity;

Diabetes or complications of diabetes;

Inflammatory diseases such as arthritis;

Respiratory diseases such as asthma;

Regulation of hormone release for example from the pituitary.

When for example well-known drugs effective against hypertension such as $\beta$-blockers are used to control the blood pressure, the raised level of NPY is not normalized. This phenomenon is anticipated to be one important reason for the increased incidence of people with high blood pressure to get secondary cardiovascular complications. There are no compounds known to antagonize NPY or the effects of NPY.

According to the present invention it has surprisingly become possible to overcome and reduce the above mentioned disorders by the use of at least one isomer of inositoltrisphosphate ($IP_3$) for the preparing of a medicament for preventing, alleviating or combatting these diseases and conditions in mammals including man.

In preferred embodiments of the invention the medicament is intended to be used as an NPY-antagonist. In other preferred embodiments of the invention the medicament is intended to be used for preventing, alleviating or combatting diseases pertaining to the heart, blood vessels, the renal system or cerebral diseases.

In addition the present invention relates to a pharmaceutical composition comprising at least one isomer of inositoltrisphosphate ($IP_3$) in combination with a pharmaceutically active compound effective in the cardiovascular, renal and/or cerebral area.

The invention also covers the use of inositoltrisphosphate ($IP_3$) in combination with another pharmaceutically active compound for preparing of a medicament for preventing, alleviating or combatting diseases pertaining to the cardiovascular, renal and cerebral diseases in mammals including man.

From the European Patent No. 179439 a pharmaceutical composition comprising as a pharmaceutically active ingredient at least one isomer of inositoltrisphosphate is known. In said patent the effect of this pharmaceutical composition is shown for different areas, such as platelet aggregation.

The present invention relates to the use of at least one isomer of $IP_3$ for preparing a medicament for preventing, alleviating or combatting for example the following conditions:

Diseases pertaining to the heart, blood vessels or the renal system such as vasospasm, heart failure, shock, cardiac hypertrophy, increased blood pressure, angina, myocardial infarction or conditions related to myocardial infarction, sudden cardiac death, arrythmia, peripheral vascular disease and abnormal renal conditions such as impaired flow of fluid, abnormal mass transport or renal failure;

Conditions related to increased sympathetic nerve activity for example during or after coronary artery surgery and operations and surgery in the gastrointestinal tract;

Cerebral diseases and diseases related to the central nervous system such as cerebral infarction, stroke and conditions related to stroke, cerebral vasospasm and hemorrhage, depression and dementia;

Diseases related to abnormal gastrointestinal motility and secretion such as different forms of ileus and Crohn's disease;

Abnormal drink and food intake such as obesity, anorexia and metabolic disorders;

Respiratory diseases such as asthma and conditions related to asthma and bronchoconstriction;

Diseases related to abnormal hormone release for example leutinizing hormone, growth hormone and prolactin.

Abnormal NPY-levels or abnormal NPY-induced effects are associated with the above mentioned disorders and $IP_3$ is acting primarily as an NPY-antagonist or as an antagonist against NPY-induced effects. Peptides which are related to NPY such as peptide YY (PYY) and/or other peptides belonging to the pancreatic polypeptide-fold (PP-fold) family of regulatory peptides also occur abnormally in some of the conditions mentioned above. Under certain circumstances the effect of $IP_3$ could also be directed against properties or effects induced by these peptides. In some conditions the effects induced by for example NPY could be mediated by substances as endothelin and alike. However, the effects of $IP_3$ against the above mentioned conditions might also be mediated by mechanisms and pathways not related to the described peptides.

The production of $IP_3$ and the isolation of the different isomers thereof are disclosed in the U.S. Pat. No. 4,777,134. The $IP_3$ isomers can also be produced by synthetic methods, chemically or enzymatically, starting with e.g. inositol and a phosphorus source. Furthermore, microbiological production methods including hybrid DNA-techniques of IP$_3$ are also suitable.

The structure of IP$_3$ and the different isomers thereof are disclosed in the U.S. Pat. No. 4,735,936 and the U.S. Pat. No. 4,797,390.

It is suitable that the medicament used according to the invention exists in unit dosage form. Tablets, granules or capsules are suitable administration forms for such unit dosage. Furthermore, tablets and granules can easily be surface treated such as to provide an enteric coating to prevent an uncontrolled hydrolysis in the stomach and to bring about a desired absorption in the intestine. Other suitable administration forms are slow release and transdermal administration. A usual pharmaceutically acceptable additive, excipient and/or carrier can be included in the medicament. The tablets or granules can also contain a disintegrant which causes the tablets or the granules, respectively, to disintegrate easily in the intestine. In certain cases, especially in acute situations, it is preferable to use the unit dosage in the form of a solution for intravenous administration.

The medicament can also consist as such of IP$_3$ solely without any additive, excipient or carrier.

If desired, the medicament can be free of other inositol phosphates, IP$_1$, IP$_2$, IP$_4$, IP$_5$ and IP$_6$. Accordingly, the mixture of IP$_3$ isomers can have a purity of 90–100%, such as 93–100% or preferably 95–100%.

Alternatively, the medicament can consist of or comprise one or more specific IP$_3$ isomers, each present in substantially pure form. Thus, the different isomers can be isolated from each other in substantially pure form, which means that they have a purity of 80–100%, such as 82–100% or 85–100%, preferably 90–100%. Since the isomers can be produced in pure form they can be mixed in any proportion, of course.

The medicament can consist of IP$_3$, wherein said IP$_3$ is provided by at least one of IP$_6$, IP$_5$ or IP$_4$ and a degradative substance such as an enzyme suitable to form IP$_3$.

It is in most cases suitable that the IP$_3$-isomer or isomers used for the preparing of the medicament according to the invention are present in salt form in order not to affect the mineral balance negatively. The salt should preferably consist of a sodium, potassium, calcium, zinc or magnesium salt or a mixture of two or more of these salts.

For the above mentioned reasons it is also an advantage if the medicament contains a surplus or an extra addition of at least one pharmaceutically acceptable salt of calcium, zinc or magnesium with a mineral acid or organic acid. This is especially valuable for elderly persons who are often deficient in these minerals.

For administration to human patients appropriate dosages can routinely be determined by those skilled in this art by extension of the results obtained in animals at various dosages. The preferred dosage for humans falls within the range of 0.1 to 1000 mg, especially 0.1–200 mg IP$_3$/day/kg body weight.

In animal experiments, no toxic effects were seen after administration of very high doses of IP$_3$, 160 mg/kg body weight by intraperitoneal injection to mice.

The medicament usually contains 0.01–1.5 g, such as 0.05–1.3 g or preferably 0.1–1 g of IP$_3$ per unit dosage.

The composition used according to the present invention contains at least one, sometimes two or more of the following substances, which correspond to the essential IP$_3$-isomer or isomers mentioned above:

D-myo-inositol-1,2,6-trisphosphate of the formula

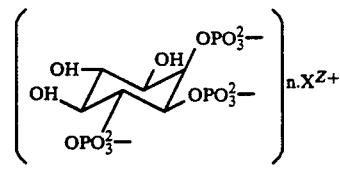

where X is hydrogen, at least one univalent, divalent or multivalent cation, or a mixture thereof, n is the number of ions, and z is the charge of the respective ion;

myo-inositol-1,2,3.-trisphosphate of the formula

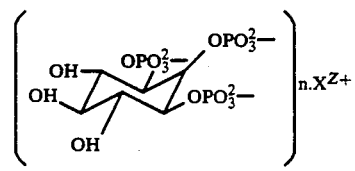

where X, n and z have the above mentioned meaning;

L-myo-inositol-1,3,4-trisphosphate of the formula

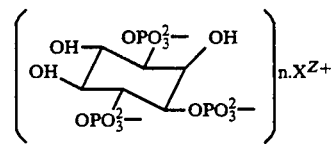

where X, n and z have the above mentioned meaning.

In each of the above formulas n ranges between 6 to 1 inclusive and z ranges from 1 to 6 inclusive. Preferably, n is between 3 to 6 inclusive and z is 3, 2 or 1. Of the above isomers D-myo-inositol-1,2,6-trisphosphate is preferred.

Other inositol trisphosphate isomers that may be utilized in the present invention as the active IP$_3$ ingredient in the composition have the structural formula

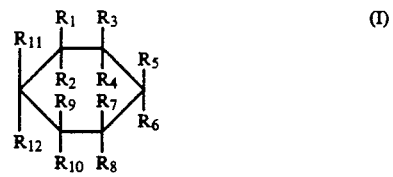

(I)

One group of inositol trisphosphate compound is defined by the structural formula (I) where three of R$_1$, R$_3$, R$_5$, R$_7$, R$_{10}$ and R$_{11}$ are hydroxyl and the remaining three are phosphate and R$_2$, R$_4$, R$_6$, R$_8$, R$_9$ and R$_{12}$ are hydrogen.

Another group of inositol trisphosphates is defined by the structural formula (I) where three of R$_1$, R$_3$, R$_6$, R$_7$, R$_9$ and R$_{12}$ are hydroxyl and the remaining three are phosphate and R$_2$, R$_4$, R$_5$, R$_8$, R$_{10}$ and R$_{11}$ are hydrogen.

Still another group of inositol trisphosphates is defined by the structural formula (I) where three of R$_1$, R$_3$, R$_5$, R$_8$, R$_{10}$ and R$_{12}$ are hydroxyl and the remaining three are phosphate and $R_2$, $R_4$, $R_6$, $R_7$, $R_9$ and $R_{11}$ are hydrogen.

Yet another group of inositol trisphosphates is defined by the structural formula (I) where three of $R_1$, $R_4$, $R_5$, $R_8$, $R_9$ and $R_{12}$ are hydroxyl and the remaining three are phosphate and $R_2$, $R_3$, $R_6$, $R_7$, $R_{10}$ and $R_{11}$ are hydrogen.

Still yet another group of inositol trisphosphates is defined by the structural formula (I) where three of $R_1$, $R_3$, $R_6$, $R_8$, $R_9$ and $R_{12}$ are hydroxyl and the remaining three are phosphate and $R_2$, $R_4$, $R_5$, $R_7$, $R_{10}$ and $R_{11}$ are hydrogen.

Even still another group of inositol trisphosphates is defined by the structural formula (I) where three of $R_1$, $R_3$, $R_6$, $R_7$, $R_{10}$ and $R_{12}$ are hydroxyl and the remaining three are phosphate and $R_2$, $R_4$, $R_5$, $R_8$, $R_9$ and $R_{11}$ are hydrogen.

Even yet another group of inositol trisphosphates is defined by the structural formula (I) where three of $R_1$, $R_3$, $R_5$, $R_8$, $R_{10}$ and $R_{11}$ are hydroxyl and the remaining three are phosphate and $R_2$, $R_4$, $R_6$, $R_7$, $R_9$ and $R_{12}$ are hydrogen.

Finally, another group of inositol trisphosphates is defined by the structural formula (I) where three of $R_1$, $R_3$, $R_5$, $R_7$, $R_9$ and $R_{11}$ are hydroxyl and the remaining three are phosphate and $R_2$, $R_4$, $R_6$, $R_8$, $R_{10}$ and $R_{12}$ are hydrogen.

Particular inositol trisphosphate compounds within the contemplation of the above formula include compounds having the structural formula (I) where $R_5$, $R_7$ and $R_{10}$ are phosphate, $R_1$, $R_3$ and $R_{11}$ are hydroxyl and $R_2$, $R_4$, $R_6$, $R_8$, $R_9$ and $R_{12}$ are hydrogen;

$R_1$, $R_{10}$ and $R_{11}$ are phosphate, $R_3$, $R_5$ and $R_7$ are hydroxyl and $R_2$, $R_4$, $R_6$, $R_8$, $R_9$ and $R_{12}$ are hydrogen;

$R_1$, $R_3$ and $R_{11}$ are phosphate, $R_5$, $R_7$ and $R_{10}$ are hydroxyl and $R_2$, $R_4$, $R_6$, $R_8$, $R_9$ and $R_{12}$ are hydrogen;

$R_3$, $R_5$ and $R_7$ are phosphate, $R_1$, $R_{10}$ and $R_{11}$ are hydroxyl and $R_2$, $R_4$, $R_6$, $R_8$, $R_9$ and $R_{12}$ are hydrogen;

$R_3$, $R_7$ and $R_{10}$ are phosphate, $R_1$, $R_5$ and $R_{11}$ are hydroxyl and $R_2$, $R_4$, $R_6$, $R_8$, $R_9$ and $R_{12}$ are hydrogen;

$R_3$, $R_{10}$ and $R_{11}$ are phosphate, $R_1$, $R_5$ and $R_7$ are hydroxyl and $R_2$, $R_4$, $R_6$, $R_8$, $R_9$ and $R_{12}$ are hydrogen;

$R_1$, $R_3$ and $R_6$ are phosphate, $R_7$, $R_9$ and $R_{12}$ are hydroxyl and $R_2$, $R_4$, $R_5$, $R_8$, $R_{10}$ and $R_{11}$ are hydrogen;

$R_6$, $R_7$ and $R_9$ are phosphate, $R_1$, $R_3$ and $R_{12}$ are hydroxyl and $R_2$, $R_4$, $R_5$, $R_8$, $R_{10}$ and $R_{11}$ are hydrogen;

$R_3$, $R_5$ and $R_8$ are phosphate, $R_1$, $R_{10}$ and $R_{12}$ are hydroxyl and $R_2$, $R_4$, $R_6$, $R_7$, $R_9$ and $R_{11}$ are hydrogen;

$R_1$, $R_3$ and $R_{12}$ are phosphate, $R_5$, $R_8$ and $R_{10}$ are hydroxyl and $R_2$, $R_4$, $R_6$, $R_7$, $R_9$ and $R_{11}$ are hydrogen;

$R_1$, $R_3$ and $R_5$ are phosphate, $R_8$, $R_{10}$ and $R_{12}$ are hydroxyl and $R_2$, $R_4$, $R_6$, $R_7$, $R_9$ and $R_{11}$ are hydrogen;

$R_1$, $R_5$ and $R_8$ are phosphate, $R_3$, $R_{10}$ and $R_{12}$ are hydroxyl and $R_2$, $R_4$, $R_6$, $R_7$, $R_9$ and $R_{11}$ are hydrogen;

$R_1$, $R_5$ and $R_{12}$ are phosphate, $R_3$, $R_8$ and $R_{10}$ are hydroxyl and $R_2$, $R_4$, $R_6$, $R_7$, $R_9$ and $R_{11}$ are hydrogen;

$R_1$, $R_3$ and $R_{12}$ are phosphate, $R_6$, $R_8$ and $R_9$ are hydroxyl and $R_2$, $R_4$, $R_5$, $R_7$, $R_{10}$ and $R_{11}$ are hydrogen;

$R_1$, $R_3$ and $R_6$ are phosphate, $R_7$, $R_{10}$ and $R_{12}$ are hydroxyl and $R_2$, $R_4$, $R_5$, $R_8$, $R_9$ and $R_{11}$ are hydrogen;

$R_4$, $R_5$ and $R_8$ are phosphate, $R_1$, $R_9$ and $R_{12}$ are hydroxyl and $R_2$, $R_3$, $R_6$, $R_7$, $R_{10}$ and $R_{11}$ are hydrogen;

$R_3$, $R_5$ and $R_8$ are phosphate, $R_1$, $R_{10}$ and $R_{11}$ are hydroxyl and $R_2$, $R_4$, $R_6$, $R_7$, $R_9$ and $R_{12}$ are hydrogen;

$R_1$, $R_3$ and $R_5$ are phosphate, $R_8$, $R_{10}$ and $R_{11}$ are hydroxyl and $R_2$, $R_4$, $R_6$, $R_7$, $R_9$ and $R_{12}$ are hydrogen;

$R_1$, $R_3$ and $R_5$ are phosphate, $R_7$, $R_9$ and $R_{11}$ are hydroxyl and $R_2$, $R_4$, $R_6$, $R_8$, $R_{10}$ and $R_{12}$ are hydrogen;

$R_1$, $R_3$ and $R_{12}$ are phosphate, $R_5$, $R_8$ and $R_9$ are hydroxyl and $R_2$, $R_4$, $R_6$, $R_7$, $R_{10}$ and $R_{11}$ are hydrogen;

$R_1$, $R_3$ and $R_8$ are phosphate, $R_5$, $R_9$ and $R_{12}$ are hydroxyl and $R_2$, $R_4$, $R_6$, $R_7$, $R_{10}$ and $R_{11}$ are hydrogen;

$R_3$, $R_5$ and $R_{12}$ are phosphate, $R_1$, $R_8$ and $R_9$ are hydroxyl and $R_2$, $R_4$, $R_6$, $R_7$, $R_{10}$ and $R_{11}$ are hydrogen;

$R_1$, $R_5$ and $R_9$ are phosphate, $R_3$, $R_8$ and $R_{12}$ are hydroxyl and $R_2$, $R_4$, $R_6$, $R_7$, $R_{10}$ and $R_{11}$ are hydrogen;

$R_1$, $R_5$ and $R_{12}$ are phosphate, $R_3$, $R_8$ and $R_9$ are hydroxyl and $R_2$, $R_4$, $R_6$, $R_7$, $R_{10}$ and $R_{11}$ are hydrogen;

$R_1$, $R_3$ and $R_9$ are phosphate, $R_5$, $R_8$ and $R_{12}$ are hydroxyl and $R_2$, $R_4$, $R_6$, $R_7$, $R_{10}$ and $R_{11}$ are hydrogen;

$R_3$, $R_5$ and $R_9$ are phosphate, $R_1$, $R_8$ and $R_{12}$ are hydroxyl and $R_2$, $R_4$, $R_6$, $R_7$, $R_{10}$ and $R_{11}$ are hydrogen;

$R_5$, $R_9$ and $R_{12}$ are phosphate, $R_1$, $R_3$ and $R_8$ are hydroxyl and $R_2$, $R_4$, $R_6$, $R_7$, $R_{10}$ and $R_{11}$ are hydrogen;

$R_1$, $R_8$ and $R_9$ are phosphate, $R_3$, $R_5$ and $R_{12}$ are hydroxyl and $R_2$, $R_4$, $R_6$, $R_7$, $R_{10}$ and $R_{11}$ are hydrogen;

$R_1$, $R_8$ and $R_{12}$ are phosphate, $R_3$, $R_5$ and $R_9$ are hydroxyl and $R_2$, $R_4$, $R_6$, $R_7$, $R_{10}$ and $R_{11}$ are hydrogen;

$R_5$, $R_8$ and $R_{12}$ are phosphate, $R_1$, $R_3$ and $R_9$ are hydroxyl and $R_2$, $R_4$, $R_6$, $R_7$, $R_{10}$ and $R_{11}$ are hydrogen;

$R_1$, $R_9$ and $R_{12}$ are phosphate, $R_3$, $R_5$ and $R_8$ are hydroxyl and $R_2$, $R_4$, $R_6$, $R_7$, $R_{10}$ and $R_{11}$ are hydrogen;

$R_5$, $R_8$ and $R_9$ are phosphate, $R_1$, $R_3$ and $R_{12}$ are hydroxyl and $R_2$, $R_4$, $R_6$, $R_7$, $R_{10}$ and $R_{11}$ are hydrogen;

$R_3$, $R_8$ and $R_9$ are phosphate, $R_1$, $R_5$ and $R_{12}$ are hydroxyl and $R_2$, $R_4$, $R_6$, $R_7$, $R_{10}$ and $R_{11}$ are hydrogen;

$R_3$, $R_9$ and $R_{12}$ are phosphate, $R_1$, $R_5$ and $R_8$ are hydroxyl and $R_2$, $R_4$, $R_6$, $R_7$, $R_{10}$ and $R_{11}$ are hydrogen;

$R_3$, $R_8$ and $R_{12}$ are phosphate, $R_1$, $R_5$ and $R_9$ are hydroxyl and $R_2$, $R_4$, $R_6$, $R_7$, $R_{10}$ and $R_{11}$ are hydrogen; and $R_8$, $R_9$ and $R_{12}$ are phosphate, $R_1$, $R_3$ and $R_5$ are hydroxyl and $R_2$, $R_4$, $R_6$, $R_7$, $R_{10}$ and $R_{11}$ are hydrogen.

The above formula describes specific isomers of inositol trisphosphate where the inositol is selected from the group myoinositol, cisinositol, epiinositol, alloinositol, neoinositol, mucoinositol, chiroinositol and scylloinositol.

The present invention also relates to a pharmaceutical composition comprising at least one specific isomer of $IP_3$ and a pharmaceutically active compound effective in the cardiovascular, renal and/or cerebral area. The other pharmaceutically active compound is for example selected from the group of α-adrenergic blocking agents, β-adrenergic blocking agents, calcium-channel blockers, ACE-inhibitors and diuretics.

As specific examples of this type of compounds the following could be mentioned:

Phenoxybenzamine, phentolamine, tolazoline, prazosin, chlorpromazine and haloperidol; propranolol, nadolol, timolol, pindolol, metoprolol and atenolol; verapamil, nifedipine and diltiazem; captopril and enalapril; acetazolamide, dichlorpheriamide, benzthiazide, furosemide, bumetanide and amiloride.

In one preferred embodiment of the invention $IP_3$ is administered together with another pharmaceutically active compound in order to control the blood pressure.

When the medicament is prepared from $IP_3$ and at least one other pharmaceutically active ingredient the dosage form could be combined or separate for separate or combined administration.

The invention will be further explained in connection with the following examples. Example 1 shows the counteractive effect of $IP_3$ against NPY-induced vasoconstriction. Example 2 demonstrates the reduction of NPY-induced hypertension in vivo when $IP_3$ is administered. Example 3 illustrates the preparation of an injectable solution of IP$_3$. Example 4 shows the counteractive effect of IP$_3$ against NPY-induced food intake. In example 5 the combination therapy of IP$_3$ and an ACE-inhibitor is demonstrated in reducing high blood pressure.

EXAMPLE 1

The basilar arteries from guinea pigs were dissected free and were then cut into cylindrical segments (2-3 mm long; 0.2-0.3 mm outer diameter) before the experiments started. Each segment was mounted on two L-shaped metal prongs, where one was connected to a force displacement transducer for continuous recording of the tension and the other to a displacement device.

The mounted specimens were immersed in tissue baths (37° C.) containing a buffer solution of the following composition (mM) and pH 7.4: sodium chloride, 119; sodium hydrogen carbonate, 15; potassium chloride, 4.6; magnesium chloride, 1.2; sodium dihydrogen phosphate, 1.2; calcium chloride, 1.5; glucose, 11.

A tension of 2 mN was applied to the arterial segments and the contractile capacity of each vessel segment was examined by exposure to a potassium-rich (60 mM) buffer solution. The maximum contraction obtained in this way was given the value 100%.

The NPY-induced contraction was measured after dissolving NPY in the above mentioned buffer to a final concentration of 0.3 $\mu$M NPY.

The antagonistic properties of D-myo-inositol-1.2.6-trisphosphate (IP$_3$) in this system were evaluated by incubation with different concentrations of IP$_3$ twenty minutes before the addition of NPY to the tissue bath.

The following results were obtained:

| Compound | Contraction (%) |
|---|---|
| NPY, no IP$_3$ | 76.4 |
| NPY + IP$_3$ (10$^{-8}$M) | 55.8 |
| NPY + IP$_3$ (10$^{-7}$M) | 39.6 |
| NPY + IP$_3$ (10$^{-6}$M) | 25.6 |

IP$_3$ demonstrates a significant decrease of the vasoconstriction induced by NPY also in very low concentrations. These effects imply a very potent inhibition of vessel constriction, which is a dominant component in diseases and conditions such as vasospasm, angina, stroke and hypertension.

EXAMPLE 2

In this experiment rats were used for an in vivo evaluation of the effects of NPY.

The animals were anaesthetized with pentobarbital and operated in such a way that the peripheral vasoconstriction can be studied without the normal compensatory behaviour of the central nervous system. Thus in this model direct effects for example on blood pressure when introducing substances influencing vasoconstriction can be measured.

Six animals were used as a control group. These animals were given an injection of saline just before another injection of 1 mg/kg NPY. The medium blood pressure after the injection of NPY was measured to be 70 mm Hg.

To six other animals were given an injection of 20 mg/kg of D-myo-inositol-1,2,6-trisphosphate (IP$_3$) before the injection of NPY. Determination of the medium blood pressure in this group of animals gave a value of 15 mm Hg.

Thus IP$_3$ shows a significant effect on reducing NPY-induced vasoconstriction. These effects demonstrate a very potent effect of IP$_3$ to reduce vasoconstriction which is very beneficial in conditions like stroke, vasospasm and hypertension.

EXAMPLE 3

Solution of sodium salt of D-myo-inositol-1,2,6-trisphosphate for injection.

0.5 g of the sodium salt of IP$_3$ and 0.77 g NaCl were dissolved in 98.73 ml of water for injection to form a solution suitable for injection into a person or an animal.

EXAMPLE 4

The experiment was designed in order to register food intake when neuropeptide Y (NPY) and saline or D-myo-inositol-1,2,6-trisphosphate (IP$_3$) were administered in rats. Rats under anesthesia were stereotactically implanted with chronic guide cannulas ending in the right lateral cerebral ventricle. The cannulas were fixed to the skull with screws and dental cement and closed with an obturator when not used. The rats were allowed to recover at least a week before the experiment started. Injections of saline or IP$_3$ were injected 15 minutes before the injection of NPY. Immediately after the first injection the rats were placed in separate cages equipped with a standard amount of food (25 g). The food intake for each animal was registered 5 hours after the injections. The data obtained are shown in the following table:

| | Food intake (g) |
|---|---|
| Saline and NPY (2 nmol) | 10.1 ± 0.7 |
| IP$_3$ (200 nmol) and NPY (2 nmol) | 5.6 ± 0.6 |

When IP$_3$ was administered the NPY induced hyperphagia was significantly reduced which describes the potent effect of IP$_3$ in food intake-related disorders.

EXAMPLE 5

The effects of sympathetic nerve stimulation on vasoconstrictor responses of norepinephrine and neuropeptide Y (NPY) were studied in the dog gracilis muscle in vivo. The addition of an angiotensin converting enzyme (ACE)-inhibitor and D-myoinositol-1,2,6-trisphosphate (IP$_3$) was made in order to observe their respective effects on the above mentioned components on vasoconstrictor responses.

Female Beagle dogs were anaesthetized with sodium pentobarbitone (30 mg kg$^{-1}$ intravenously (i.v.) followed by 3.5 mg kg$^{-1}$ i.v.) and artificially ventilated. Catheters were placed in the cartoid artery for systemic blood pressure monitoring and in the brachial veins for administration of compounds and fluid replacement.

The gracilis muscles were isolated and heparin was given (1000 U kg$^{-1}$ i.v. followed by 400 U kg$^{-1}$ h$^{-1}$) and the tissues were perfused with blood from the femoral artery at constant flow by means of a roller pump, adjusted to give a perfusion pressure of approximately 100 mm Hg. Blood pressures were recorded by Statham P23Ac tranducers and were displayed on a Grass model 7C polygraph.

The gracilis nerves were stimulated via bipolar platinum electrodes at constant frequencies using Grass model S6 stimulators. This stimulation results in an increased blood pressure which comprises different components. One dominant component is regulated by norepinephrine while another dominant component is regulated by NPY. Nerve stimulations were initially performed before administration of any compound in order to give control values. The increase in blood pressure was measured directly and 2, 5 and 10 minutes after stimulation. Following the control measurements the ACE-inhibitor benazeprilat (10 mg i.v.) was administered. The increase in blood pressure was again measured starting 20 minutes after the administration. After these measurements, while the ACE-inhibitor was still in the circulation of the animal, IP$_3$ (500 $\mu$M i.v.) was administered. The increase in blood pressure was again determined starting 10 minutes after the last dosage in order to obtain the increase in blood pressure after the combined dosage. Blood pressure was continuously monitored throughout the experiment. With this experimental set-up it was possible to obtain control data, data after distribution of the ACE-inhibitor per se and in combination with IP$_3$.

The results are shown in the following table:

|  | Minutes after stimulation | | | |
| --- | --- | --- | --- | --- |
|  | 0 | 2 | 5 | 10 |
|  | Increase in blood pressure (mm Hg) | | | |
| Control | 0 | 106 | 90 | 55 |
| ACE-inhib. | 0 | 42 | 33 | 19 |
| ACE-inhib. and IP$_3$ | 0 | 24 | 17 | 7 |

The results show that the ACE-inhibitor reduced the norepinephrine-induced increase of blood pressure. The combined dosage with IP$_3$ reduced also to a large extent the NPY-induced increase of blood pressure. These data demonstrate the beneficial effect of using a combined therapy in order to reduce vasoconstriction induced by norepinephrine and NPY.

EXAMPLE 6

The effect of D-myo-inositol-1,2,6-trisphosphate (IP$_3$) to reduce gastrointestinal secretion was assessed in an experiment with rats.

Two groups of 9 animals in each were deprived of food 12 hrs before the experiment and were then anesthesized with pentobarbital (Nembutal ®, 50 mg/kg). After a surgical operation in the gastrointestinal tract a 10 cm long jejunal segment was isolated with intact vascular supply. This segment, still in normal contact with the animal, was placed in a plastic chamber in such a way that the free passage of fluid in and out of the segment was allowed. The chamber was hanging approximately 5 mm above the abdominal wall of the animal and was connected to a force displacement transducer for measuring changes in intestinal weight. Net fluid transport (NFT) across the intestinal segment was continuously recorded by connecting the force transducer to a Grass polygraph.

Pure cholera toxin (Sigma Chemicals), 20 $\mu$g, were dissolved in 0.5 ml saline (0.9% NaCl-solution) and was introduced into the intestinal lumen in each animal. Within three hours all animals developed a net fluid loss from the intestinal tissue into the lumen. After this period an infusion of IP$_3$ (60 mg/kg h) was administered to one group of the animals while the other group received saline via infusion.

The secretion from the intestinal segment, net fluid transport (NFT), measured as $\mu$l/min$\times$100 cm$^2$, was determined for 30 minute periods during the infusion.

The data obtained are shown in the following table:

| | NFT ($\mu$l/min $\times$ 100 cm$^2$) | |
| --- | --- | --- |
| Time period after infusion. start (mins) | Control group | IP$_3$-treated group |
| before infusion | 124 | 90 |
| 0–30 | 115 | 16 |
| 30–60 | 105 | 8 |
| 60–90 | 99 | 12 |
| 90–120 | 97 | 15 |
| 120–150 | 105 | 24 |
| 150–180 | 108 | 13 |

Thus a dramatic decrease in gastrointestinal secretion (diarrhoea) is achieved when treatment with IP$_3$ is performed.

We claim:

1. A method of preventing, alleviating or combatting diseases related to abnormal gastrointestinal motility and secretion in a mammal including man comprising administering to a mammal in need thereof a pharmaceutically effective amount of at least one isomer of inositoltriphosphate or a pharmaceutically acceptable salt thereof.

2. The method according to claim 1 wherein said pharmaceutically acceptable salt is a salt of sodium, potassium, calcium or zinc.

3. The method according to claim 1 wherein said at least one isomer of inositoltrisphosphate is administered in unit dosage forms comprising tablets, granules and solutions.

4. The method according to claim 3 wherein said unit dosage is from about 0.01 to about 1.5 g.

5. The method according to claim 4 wherein said unit dosage is from about 0.05 to about 1.3 g.

6. The method according to claim 1 wherein said at least one isomer of inositoltrisphosphate or pharmaceutically acceptable salt thereof is administered at a dosage of about 0.1 to about 1000 mg/day/kg body weight of human.

7. The method according to claim 6 wherein said dosage is from about 0.1 to about 200 mg/day/kg body weight of human.

8. The method according to claim 6 wherein said pharmaceutically acceptable salt is a salt of sodium, potassium, calcium or zinc.

9. The method according to claim 2 wherein said pharmaceutically acceptable salt is administered in unit dosage forms comprising tablets, granules and solutions.

10. The method according to claim 1 wherein said inositoltrisphosphate is D-myo-inositol-1,2,6-trisphosphate.

11. The method according to claim 2 wherein said inositoltrisphosphate is D-myo-inositol-1,2,6-trisphosphate.

12. The method according to claim 6 wherein said inositoltrisphosphate is D-myo-inositol-1,2,6-trisphosphate.

13. The method according to claim 1 wherein said disease is a form of ileus.

14. The method according to claim 1 wherein said disease is Crohn's disease.

* * * * *